United States Patent [19]
Cantoro

[11] Patent Number: 5,770,628
[45] Date of Patent: Jun. 23, 1998

[54] OPHTHALMIC PREPARATION FOR USE AS ARTIFICIAL TEAR

[75] Inventor: Amalio Cantoro, Bologna, Italy

[73] Assignee: Laboratoire Medidom S.A., Geneva, Switzerland

[21] Appl. No.: 505,095

[22] Filed: Jul. 21, 1995

[30] Foreign Application Priority Data

Jul. 25, 1994 [IT] Italy ................................ RM94A0485

[51] Int. Cl.$^6$ ........................... A61K 31/74; A01N 59/26
[52] U.S. Cl. ....................... 514/778; 424/78.04; 424/427; 514/53; 514/777; 514/915
[58] Field of Search ................................ 424/78.04, 422, 424/427, 600, 601, 610, 611, 617, 677, 678, 679, 680, 681, 682; 514/54, 62, 777, 915

[56] References Cited

U.S. PATENT DOCUMENTS

| | | | |
|---|---|---|---|
| 4,409,205 | 10/1983 | Shively | 424/78 |
| 5,106,615 | 4/1992 | Dikstein | 424/78.04 |
| 5,166,331 | 11/1992 | Della Valle et al. | 536/55.1 |
| 5,409,904 | 4/1995 | Hecht et al. | 514/23 |

FOREIGN PATENT DOCUMENTS

| | | |
|---|---|---|
| 0205279 | 12/1986 | European Pat. Off. |
| 0323522 | 7/1989 | European Pat. Off. |
| 0414373 | 2/1991 | European Pat. Off. |
| 8404681 | 12/1984 | WIPO |

OTHER PUBLICATIONS

Bachman et al., Essential Ions for Maintenance of the Corneal Epithelial Surface:, Invest. Opthalmal. Vis. Sci., 26, 1484–88 (1985).

Risomondo et al., "Electrolyte Composition of Lacrimal Gland Fluid and Tears of Normal and Vitamin A—Deficient Rabbits" CLAO J 15(3), 222–229 (1989).

Green et al., "Tear Potassium Contribute to Maintenance of Corneal Thickness", Opthalmic Res. 24, 99–102 (1992).

Iwata, The Preocular Tear Film and the Dry Eye Syndrome, Intl. Ophthalmology Clinis, Holly and Lemp, eds., Little Brown, 31–32, (1973).

Rolando et al., "The Effect of Hyphosmolarity on Tear Mueus Ferning", Fortschr Opthalmol, 83, 644–646 (1986).

Nelson, "Impression Cytology", Cornea 7(1), 71–81 (1988).

*Primary Examiner*—Joseph L. Schoffer
*Assistant Examiner*—Kathryne E. Shelborne
*Attorney, Agent, or Firm*—Abelman, Frayne & Schwab

[57] ABSTRACT

Ophthalmic preparation for use as artificial tear containing hyaluronate as a viscosity thickener, preferably in the form of sodic salt and having a molecular weight of 500,000 to 4,000,000 daltons, at a concentration of 0.05 to 2% by weight, as well as the following minimum quantities of ionic species: 40 mmol/l sodium ion, 12 mmol/l potassium ion, 0.4 mmol/l calcium ion, 0.4 mmol/l magnesium ion, 50 mmol/l chloride ion, 7 mmol/l phosphate ion and, preferably, 0.7 mmol/l citrate ion. The formulation, which as an osmolarity of 140 to 280 mOsm/l, is useful for the treatment of keratoconjunctivitis sicca and may be administered whenever the use of artifical tears is advisable, e.g. for the treatment of eye irritations caused by environmental conditions or contact lenses.

33 Claims, 8 Drawing Sheets

OPHTHALMIC PREPARATION FOR USE AS ARTIFICIAL TEAR

BACKGROUND OF THE INVENTION

1. Field of the Invention

The present invention relates to an ophthalmic preparation for use as artificial tear. More precisely, the invention relates to an aqueous formulation to be instilled in the conjunctival sac for the treatment of a tear film disease known as keratoconjunctivitis sicca or dry eye syndrome and, in general, to be administered whenever the use of artifical tears is advisable, e.g. for the treatment of eye irritations such as those caused by environmental conditions or contact lenses.

The studies conducted in this area provided evidence that the tear film is a complex three-layer structure, consisting of:

- an inner mucin layer, consisting of a mixture of glycoproteins produced by conjuctival goblet cells, which is adsorbed on the corneal surface to form a hydrophilic coat;
- an intermediate aqueous layer, which spreads over said hydrophilic coat, mainly consisting of water, electrolytes, proteins, enzymes, and mucin;
- a thin external lipidic layer, whose main function is to regulate the rate of water evaporation from the tear film.

Said three-layer structure constitutes a complex physiological system, whose perfect equilibrium and continuous renewal are secured by several factors. Anomalies either of the inner mucin layer or of the intermediate aqueous layer cause the dry eye syndrome. In fact, the patients suffering from said disease show lacrimal gland fluid hyperevaporation and a reduced turnover resulting in a hyperosmotic film, whose osmolarity is as high as 330–340 mOsm/l, against a normal value of 300 mOsm/l approx.

A highly hyperosmotic lacrimal gland fluid causes the disproportion between electrolytes and high molecular weight glycoproteins (mucus) of the lacrimal gland fluid and, consequently, the absence of or a decrease in the phenomenon of mucus ferning.

In this regard, it is known that one of the most interesting physical properties of lacrimal mucus is its ability to crystallize in the form of ferns when dried by evaporation at room temperature. Ferning appears a few instants after collection of the lacrimal mucus from the fornix inferior of the eye. Although no clear evidences for the biochemical processes involved in mucus crystallization have been provided, it seems accepted that the aforesaid phenomenon is caused by the interaction between the electrolytes and that the high molecular weight glycoproteins of mucus (mucin), and that the various types of ferning (Type I, uniform; Type II, abundant with small-sized ferns and empty spaces; Type III, partial; Type IV, absent) are related to the lacrimal gland fluid being in a normal or pathological state. For example, a thick arborization is regarded as a sign of a perfect equilibrium between mucin and electrolytes; a partial tear ferning or the absence of same, which are detected in eyes suffering from keratoconjunctivitis sicca, indicate a lacrimal mucus quantitative deficiency or a qualitative alteration of glycoproteins and of their environment (pH, hydration, electrolytic equilibrium).

Furthermore, tears hyperosmolarity causes the degeneration of conjunctival cells together with exfoliation increase, loss of cellular surface microfolds, break-up of the epithelial cells membrane, and decrease in the number of mucin-producing goblet cells. Said cellular degeneration being responsible for goblet cells decrease and mucin deficiency, is regarded as the cause of most clinical symptoms of dry eye syndrome (dryness, irritation, photophobia, and foreign body sensation) and of the tear film instability.

In fact, an impaired inner mucin layer is essential for the stability of the tear film, as it improves the corneal surface wettability and increases the viscosity of the fluid phase. Should mucin be absent or insufficient, the cornea will become non-wettable and the tear film will break-up with formation of dry areas.

From a diagnostic point of view, the dry eye syndrome may not only be identified from the symptoms proper to it, but may also be detected and monitored through widely accepted procedures, such as for example the measurement of tear production (Schirmer's test), the tear film break-up time (BUT) after a wink, i.e. a complete eyelids lowering, and the evaluation of the eye surface dyeing with Rose Bengal and fluorescein. Other objective methods allowing the evaluation of the therapeutic properties of preparations for the treatment of the dry eye syndrome are the cytology by impression (or by imprint), the test of lacrimal mucus ferning and the determination of lacrimal gland fluid osmolarity. The first of said tests, which is noninvasive and repeatable, allows the examination of the morphological state of the bulbar conjunctiva cells by showing cellularity, cohesiveness, concentration of the mucus-producing goblet cells, size variation of the epithelial cells with modification of the nucleus/cytoplasm ratio, variation of cellular stratification, and epithelium keratinization, if any. Epithelium keratinization is extremely important: in fact, from a cytological point of view, one of the worst consequences of keratoconjunctivitis sicca is the progressive transformation of a secreting epithelium into a keratinized and non-secreting epithelium.

The lacrimal mucus ferning test reveals the various aspects of lacrimal mucus crystallization and classifies same according to the aforementioned types (I to IV), while the lacrimal gland fluid osmolarity values, expressed as mOsm/l, give a quantitative indication of the salt concentration in the tears, the increase of which, as already mentioned, results from an increased evaporation of the tear film water. The value of tear osmolarity may be assumed to be an objective parameter of the pathological state under consideration, since said value was found averagely to increase, in pathological conditions, by 30 to 40 mOsm/l. Keratoconjunctivitis sicca is treated not only with slow-dissolution ophthalmic preparations to be inserted into the conjunctival sac, which, however, find scarce application in so far as they are of uncomfortable application and troublesome for the patients, but also with liquid preparations to be instilled dropwise, known as artificial tears. Said artificial tears represent a correct approach to the treatment of dry eye syndrome, since they can replace natural tears, lubricate the tissues and prevent the formation of dry areas on corneal epithelial surface.

2. Description of the Prior Art

Although the artificial tears of the most common commercial formulations are physiological solutions containing, in addition to preservatives and buffers, sodium chloride alone, tests conducted on rabbit isolated corneas proved that a cornea irrigation liquid containing $K^+$, $Ca^{++}$, $Mg^{++}$, $HCO_3^-$ and $H_2PO_4^-$ ions (in addition to $Na^+$ and $Cl^-$ ions) causes a more marked decrease in epithelial cell exfoliation than sodium chloride alone and Ringer's solution (W. G. Bachaman et al., Essential ions for maintenance of the corneal epithelial surface, Invest. Ophthalmol. Vis. Sci., 26, 1484–1488, 1985).

It is widely accepted that artificial tears should be so formulated as to reproduce the quali-quantitative composition of natural tears as much as possible, with particular reference to the concentration of potassium, magnesium, calcium, chloride and bicarbonate ions (V. Rismondo et al., Electrolyte composition of lacrimal gland fluid and tears of normal and vitamin A-deficient rabbits, CLAO J. 15 (3) 222–229, 1989). In particular, potassium, which occurs in natural lacrimal gland fluid at high concentrations, is complementary to sodium in maintaining intracellular homeostasis (K. Green et al., Tear potassium contributes to maintenance of corneal thickness, Ophthalmic Res. 24, 99–102, 1992), while calcium and magnesium are cellular adhesion stabilizers. Specifically, calcium takes part in glycogen metabolism, in endocytosis processes and cellular motility (W. Y. Cheung, Calcium and cell function, Vol. 1, Academic Press, New York, 1980) while magnesium contributes to the cellular membrane permeability (S. Iwata, The preocular tear film and and dry eye syndrome, in International Ophthalmology Clinics, F. J. Holly and M. A. Lemp, eds., Little Brown, Boston, Mass. pp. 31–32, 1973) and cellular aggregation (J. K. Aikawa, The relationship of magnesium to disease in domestic animals and humans, Charles C. Thomas, Springfield, Ill., 1971).

An artificial tear formulation tending to reproduce the electrolytes combination usually occurring in lacrimal gland fluid is disclosed in European patent No. 0205279. Although such formulations supply an adequate variety of nutritive elements, essential for cellular metabolism, they have the typical drawback of the aqueous solutions containing low molecular weight salts, i.e. their viscosity is low.

That is why said solutions, once instilled in the conjunctival sac, exhibit an extremely short precorneal residence time and, therefore, are to be instilled every 10 to 15 minutes, which causes the patients' non-compliance and toxic effects on the eye tissues (conjunctiva and cornea) from the preservatives usually contained therein.

With a view to eliminating said drawback, various artificial tear formulations thickened with high molecular weight agents, usually hydrosoluble polymers of synthetic or natural origin, have been introduced in medical practice. One of said formulations, wherein the thickener is a non-ionic synthetic polymer, selected among polyvinyl alcohol, polyethylene glycol and mixtures thereof, is disclosed in U.S. Pat. No. 4,409,205.

However, the artificial tear formulation proposed therein does not comply with the aforementioned principles referring to the need for an adequate electrolytes content. In fact, said patent states that an ophthalmic solution is much more effective for bringing an irregularly structured lacrimal gland fluid back to normal if the cationic salts, in particular sodic salts, are maintained at a minimum level. Consequently, the solution claimed therein has a salt content below 0.75%, expressed as equivalents of NaCl.

Apart from the above remark, experimental investigations have established that an artificial tear has a high precorneal residence time and, at the same time, is tolerated by the patient only if thickened with an agent giving the solution non-Newtonian flow properties: this is not the case of non-ionic polymers like those proposed in the aforesaid U.S. patent.

In fact, like all Newtonian fluids, the solutions thickened with non-ionic polymeric agents, maintain a constant viscosity even if subjected to shear stress, which situation occurs in the lacrimal gland fluid during a wink. On the contrary, the glycoproteins of natural lacrimal gland fluid in an aqueous solution show a high viscosity when at rest, i.e. in the interval between two consecutive winks, and a very low viscosity during a wink, i.e. when shear stress is applied. Said Theological behaviour, which is typical of non-Newtonian fluids and in particular of the pseudoplastic ones, brings about, on the one hand, high precorneal residence times and, on the other, a good ocular tolerability. According to experimental evidences, artificial tears formulations exhibit non-Newtonian flow properties on condition that the polymeric products added thereto as thickeners are of the anionic type. An exemplary formulation meeting said criterion is described in patent application PCT No. 84/04681. The viscosity thickeners described therein are high molecular weight carboxyvinyl polymers, Carbopol type, to be added to the composition as 0.05–0.25% by weight. However, said formulation contains stabilizers, preservatives, neutralizers and preferably sodium chloride as an osmolarity regulator, but does not contain a combination of saline nutritive substances.

The polyanionic substance more frequently proposed as a viscosity thickener in ophthalmic formulations is hyarulonic acid (or the salts thereof), a polysaccharide found in several human and animal tissues. In water solution and at an adequate concentration it exhibits non-Newtonian flow properties, quite similar to those of natural tears. For example, European patent No. 0323522 proposes sodium hyaluronate (molecular weight not specified) as a thickener of an artificial tear composition, at a concentration of 0.01 to 1% by weight. However, in this case too, the proposed composition essentially contains sodium hyaluronate, sodium chloride, preservatives, and buffers, if any, but does not contain the ions essential for a physiological cellular metabolism.

Aqueous solutions containing sodium hyaluronate and a wide variety of ions are described in European patent application No. 0414373. However, said patent application is not related to preparations for artificial tears, but to viscoelastic solutions to be used in ocular surgery as adjuvants to eye microvascular surgical operations on the eye anterior section (cataract, keratoplasty, trabeculectomy) and posterior section (retina detachment, retinopathy). In eye surgery, high molecular weight sodium hyaluronate is used at a fairly high concentration to obtain products having viscoelastic properties securing, during surgical operations, the maintenance of anatomic eye spaces (e.g. anterior chamber) and, therefore, preventing the collapse of same or the separation of ocular structures or limbuses (e.g. sclera from conjunctiva), as well as the protection of eye tissues from surgical damages, if any. Although the document under consideration mentions sodium hyaluronate concentrations ranging between 0.1 and 5% by weight (preferably from 1 to 3% by weight), the viscoelastic solutions have properties suitable for the intended use only at sodium hyaluronate concentrations higher than 1% and with molecular weights of at least 1,000,000 daltons. In fact, in all embodiments described in the patent application under consideration the sodium hyaluronate concentration is 3% by weight.

Reverting to artificial tear formulations, the most recent U.S. Pat. No. 5,106,615 discloses that the solutions for cornea irrigation containing a non-Newtonian thickener at a low concentration, do not maintain said non-Newtonian behaviour because of their salt content. In particular, the U.S. patent under consideration teaches that 25 mmoles per liter of sodium chloride completely abolishes the non-Newtonian behaviour of sodium hyaluronate solutions, and that calcium, and presumably other divalent cations, is even more efficient.

Accordingly, said U.S. patent claims a formulation for use as artificial tear which maintains the advantageous rheological properties of a non-Newtonian fluid brought about by the polyanionic thickeners, only if it contains a practically negligible quantity of salts (apart from the salts of the thickener), in any case, not exceeding 1.5 mmol/l. U.S. Pat. No. 5,106,615 discloses that the formulations described in U.S. Pat. No. 4,409,205 and PCT patent application No. 84/04681 mentioned above would lose non-Newtonian flow properties due to the presence of an eccessive amount of salts.

SUMMARY

Since, in contrast with some teachings of the prior art, the presence of an adequate amount of some ionic species is assumed to be indispensable to a correct treatment of tear film diseases, it is an object of the present invention to provide a thickened composition for use as artificial tear, able to maintain non-Newtonian flow properties also in the presence of salts and precisely of bivalent cations, such as $Ca^{++}$ and $Mg^{++}$.

It is, therefore, an object of the present invention to provide a hypotonic aqueous saline solution, thickened with sodium hyaluronate and containing not only $Na^+$ and $Cl^-$ ions, but also and at least $K^+$, $Ca^{++}$, $Mg^{++}$, and $HPO_4^=$ ions, being so formulated that the non-Newtonian flow properties produced by the presence of the polymer are not negatively affected by the presence of salts. Thanks to its rheological properties, the solution proposed herein exhibits a high precorneal residence time.

Further, it significantly stabilizes the tear film by improving—as will be shown in detail hereinafter—all parameters indicative of the pathological state caused by keratoconjunctivitis sicca.

Therefore, it is a specific object of the present invention to provide an ophthalmic preparation for use as artificial tear containing a hyaluronic acid salt (hyaluronate) as a viscosity thickener at a concentration of 0.05 to 2% by weight as well as the following minimum quantities of ionic species, expressed as mmoles per liter: 40 mmol/l sodium ion, 12 mmol/l potassium ion, 0.4 mmol/l calcium ion, 0.4 mmol/l magnesium ion, 50 mmol/l chloride ion and 7 mmol/l phosphate ion and water.

Preferably, said preparation also contains a chelating agent, in particular a citrate in a quantity of at least 0.7 mmol/l and, in a preferred embodiment of the invention, has the following general formulation:

| | | | | |
|---|---|---|---|---|
| $Na^+$ | 40–95 mmol/l | $Cl^-$ | 50–150 mmol/l |
| $K^+$ | 12–28 mmol/l | $HPO_4^=$ | 7–20 mmol/l |
| $Ca^{++}$ | 0.4–1.5 mmol/l | citrate | 0.7–2.5 mmol/l |
| $Mg^{++}$ | 0.4–1.0 mmol/l | hyaluronate | 0.05–2% by weight |

Optionally, the formulation proposed herein may also contain acetate and bicarbonate ions, and EDTA as a preservative, preferably at the minimum concentrations of 7 mmol/l, 5 mmol/l, and 1 mmol/l, respectively.

DESCRIPTION OF THE PREFERRED EMBODIMENTS

The hyaluronic acid salt of the formulation is preferably sodium hyaluronate having molecular weight of 500,000 to 8,000,000 daltons, typically of 500,000 to 4,000,000 daltons. The resulting preparation is advantageously hypotonic, and has an osmolarity of 140 to 280 mOsm/l, pH of 6.8 to 7.6, viscosity of 10.0 to 200.0 cps at a shear rate of $2\ sec^{-1}$ and 10 to 5 cps at a shear rate of $1000\ sec^{-1}$, measured at 32° C.

The concentration of the hyaluronic acid salt is adjusted according to the molecular weight and the required viscosity. Molecular weight may also slighty vary with respect to the above defined values, as long as the desired viscosity and the required saline balance are obtained.

The above defined quantities and concentrations of ionic species do not include sodium ions present in the hyaluronic acid salt. Therefore, they correspond to total amounts of ionic species contained in the ophthalmic preparation for all ionic species except for sodium ions, whereas in the case of sodium ions the above defined quantities and concentrations correspond to sodium amounts in addition to those contained in sodium hyaluronate.

The sodium balance of the present ophthalmic solution may be maintained despite variations of concentration of the hyaluronic acid salt by adjusting the amounts of sodium salts other than sodium hyaluronate (for instance in the form of sodium chloride, citrate, acetate, bicarbonate, phosphates, or mixtures thereof), so to offset the reduction or (increase) in sodium from the lesser or (greater) amounts of hyaluronate. According to a typical embodiment of the present invention, sodium hyaluronate is used as the viscosity thickener, and further amounts of sodium ions are added to the opthalmic composition as sodium chloride, citrate and phosphate, so as to obtain the desired sodium ions concentration.

For practical purposes, the total amounts of sodium ions contained in the present opthalmic formulation are typically comprised between 40 and 95 mmoles per liter.

pH can be adjusted at the desired value by adding hydrochloric acid, or a base such as sodium hydroxide, as necessary, provided that the total amount of ionic species is within the scope of the present invention.

The present artificial tears are prepared according to conventional techniques by mixing the relative ingredients in appropriate amounts in sterile water, or sterilizing the formulation after its preparation.

The present formulations may also contain other conventional ingredients used in ophthalmic preparations, such as dextrose, preservatives (for instance Thimerosal®, i.e., sodium ethylmercurithiosalicylate) and the like.

The ophthalmic formulations herein diclosed and claimed represent the most favourable formulations from the point of view of both the therapeutic and the Theological properties.

As will be described in detail hereinafter, the formulation proposed herein maintains the rheological behaviour typical of the solutions based on hyaluronate in spite of the presence of relatively high quantities of various ionic species, and, when instilled in the conjunctival sac, maintains the tear osmolarity at a physiological level for more than an hour and a half after instillation. Further, it considerably assuages the symptomatology of the dry eye syndrome, improves the tear ferning pattern and the morphology of epithelial cells, and increases the density of the mucin-producing goblet cells.

Daily dosages in human therapy of the present ophthalmic formulations are of about 1–2 drops per eye, administered about 4–8 times a day (for instance by means of a standard pharmacopeial medicinal dropper of 3 mm in external diameter, which when held vertically delivers 20 drops of water of total weight of 0.9–1–1 grams at 25° C.).

The present invention will now be described in greater detail, with reference to one exemplary embodiment as set forth in the examples and illustrated in the drawings, to which the present invention is not intended to be confined.

EXAMPLE 1

Evaluation of the Rheological Properties of the Preparations of the Invention and Comparison with Other Preparations The preparation of the invention, which was subjected to the tests described hereinafter, referred to as SVS20, had the following composition:

|  | mg/100 ml | mmol/l |
|---|---|---|
| sodium hyaluronate (M.W. 800,000–1,600,000) | 250 | about 6.2[1] |
| NaCl | 279.2 | 47.77 |
| KCl | 103.3 | 13.85 |
| $Na_2HPO_4 \cdot 12H_2O$ | 322.2 | 9.0 |
| $Na_3$ citrate | 26.0 | 1.05 |
| $MgCl_2 \cdot 6H_2O$ | 9.2 | 0.45 |
| $CaCl_2 \cdot 2H_2O$ | 6.9 | 0.6 |

[1]sodium ions present in sodium hyaluronate.
pH = 7.32 and osmolarity = 150 mOsm/l; viscosity = 28 cps at a shear rate of 2 $sec^{-1}$.

With a view to comparing the rheological behaviour of said preparation with that of another artificial tear preparation thickened with hyaluronic acid and free from appreciable quantities of ionic species other than $Na^+$ and $Cl^-$, a matching preparation was developed according to European patent application No. 0323522, hereinafter referred to as SO9, having the following composition:

| sodium hyaluronate (M.W. 800,000–1,600,000) | 250 mg/100 ml |
|---|---|
| NaCl | 0.9% by weight | viscosity = 22 cps at a shear rate of 2 $sec^{-1}$.

Figure 1:
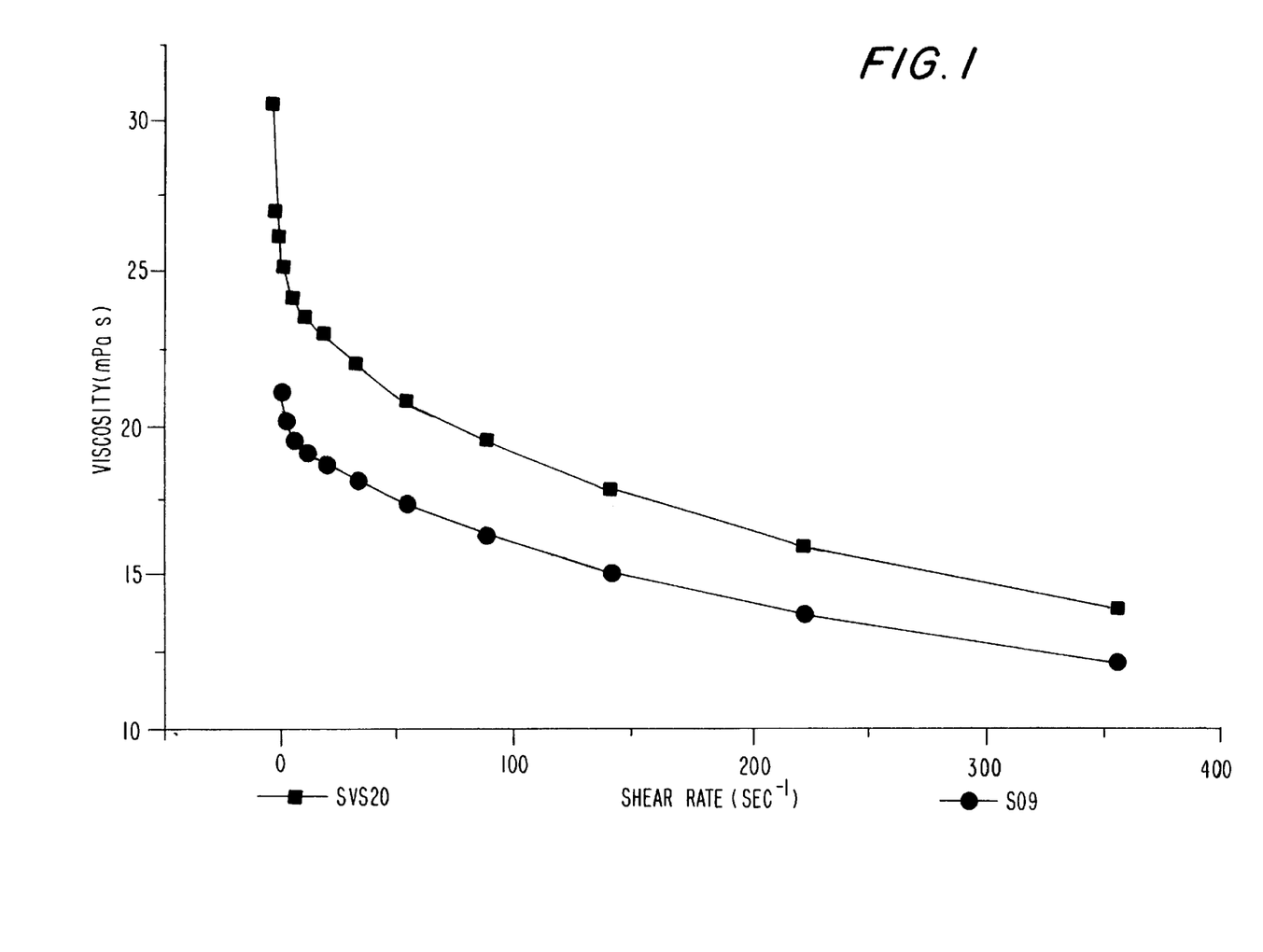
FIG. 1 shows the flow curve of viscosity as a function of share rate of a preparation of the invention and of a thickened product according to EP-0323522.
Figure 2:
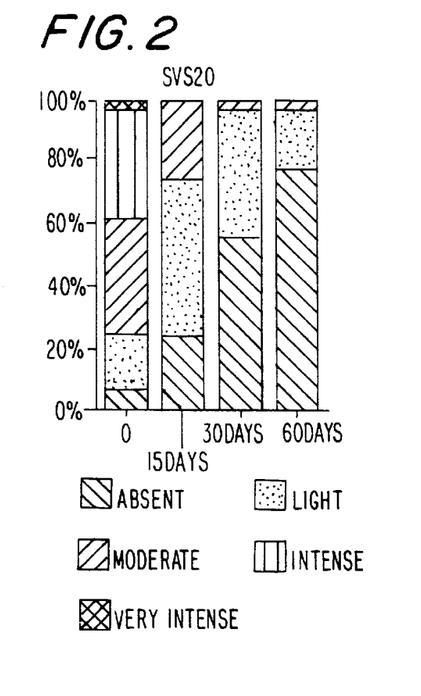
FIGS. 2 and 3 show the results of clinical trials on eye smart obtained using the preparation of the invention and a commercial product of the prior art.
Figure 3:
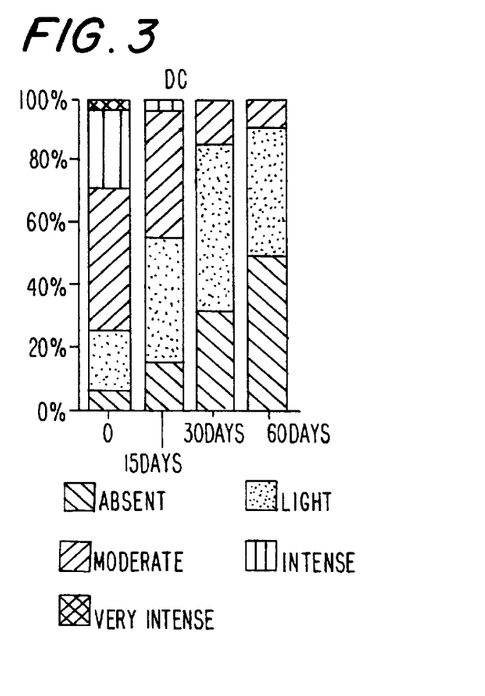
Figure 4:
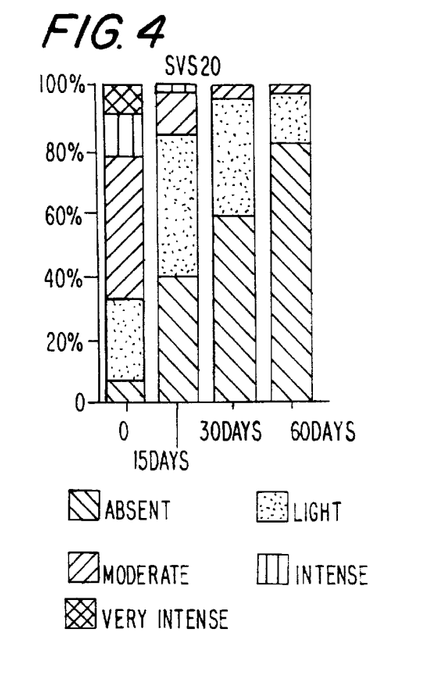
FIGS. 4 and 5 show the results of clinical trials on the foreign body sensation obtained using the preparation of the invention and the aforesaid commercial product of the prior art.
Figure 5:
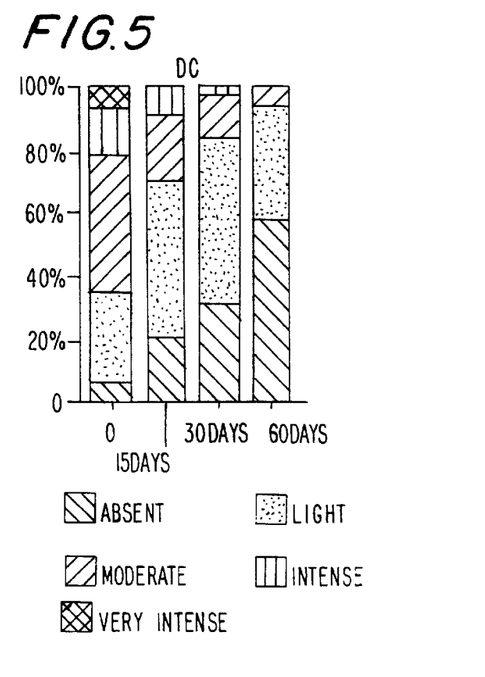
Figure 6:
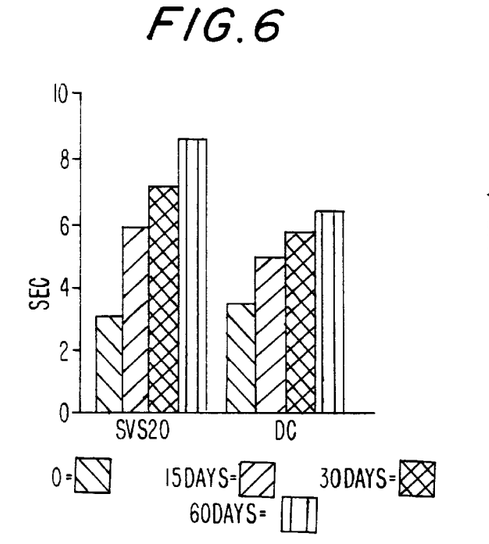
FIG. 6 shows the results of the trials on tear film break-up time (BUT) obtained using the preparation of the invention and the aforesaid commercial product of the prior art.
Figure 7:
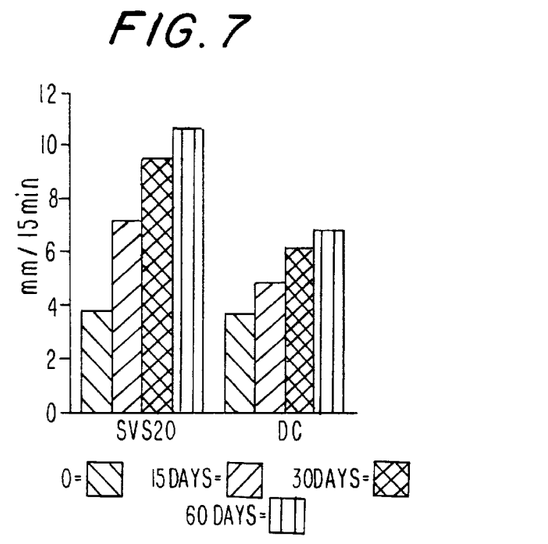
FIG. 7 shows the results of the trials on tear secretion (Shirmer I) obtained using the preparation of the invention and the aforesaid commercial product of the prior art.
Figure 8:
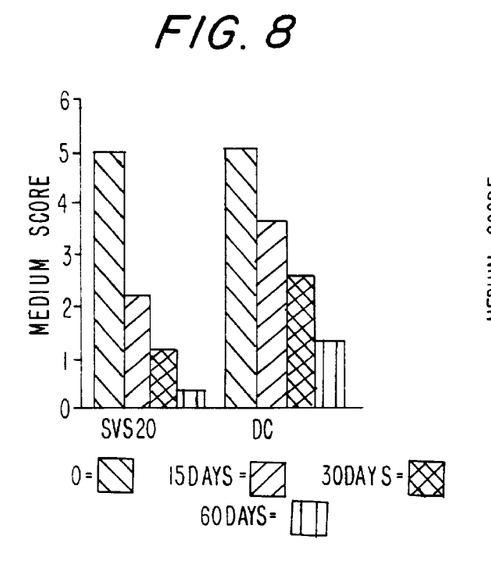
FIG. 8 shows the results of dyeing trials with fluorescein obtained using the preparation of the invention and the aforesaid commercial product of the prior art.
Figure 9:
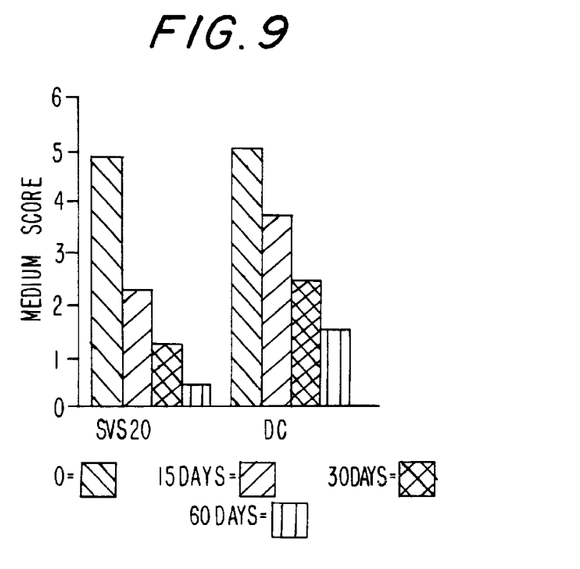
FIG. 9 shows the results of dyeing trials with Rose Bengal obtained using the preparation of the invention and the aforesaid commercial product of the prior art.

The respective flow curves (FIG. 1), where viscosity, expressed as mPa.s, is plotted versus the shear rate ($sec^{-1}$), were determined at an eye surface temperature of 32° C. to simulate the conditions of clinical use of the preparations. Measurements were carried out with a Bohlin Rheometer System viscometer, characterized by:

coaxial cylinders meter C1BC-true torsion bar 1.59 g.cm shear rate range 2–1000 $sec^{-1}$ The curves of FIG. 1 clearly show that although the viscosity of both formulations is dependent on the shear stress rate, i.e. according to a non-Newtonian behaviour (whereas, e.g., the viscosity of a formulation thickened with a non-ionic polymer is constant and, therefore, its diagram would be nearly flat), this characteristic is more pronounced in the formulation of the invention.

Therefore, although the formulation of the invention contains NaCl in an amount exceeding 25 mmoles per liter, and $K^+$ ions and bivalent cations, such as $Ca^{++}$ and $Mg^{++}$, in addition to $Na^+$, contrary to the teaching of U.S. Pat. No. 5,106,625, it does not lose its non-Newtonian properties and shows an even better non-Newtonian behaviour than a formulation exclusively containing sodium chloride as saline species.

EXAMPLE 2

Clinical Trials and Comparison with Solutions Thickened with Hydroxypropyl Methylcellulose Clinical trials were conducted with a single-dose sterile ophthalmic solution of the invention, formulated as described in Example 1 (SVS20), and comparisons were made between said solution and a commercial multidose eyedrop (eyedrop sold by ALCON under the trade name ISOPTO TEARS®, hereinafter referred to as DC), thickened with a non-ionic agent, i.e. hydroxypropyl methylcellulose, and containing an appreciable amount of sodium chloride, as the only saline species (DC composition: hydroxypropylmethylcellulose (4,000 cps) 0.5%; sodium chloride 0.1%; benzalkonium chloride 0.01%; buffering agents).

Clinical trials were conducted on 220 patients with keratoconjunctivitis sicca. 15 of them did not complete the test in so far they dropped out. The remaining 205 patients (189 women and 16 men), who completed the investigation, were randomly treated with the preparation of the invention (SVS20) or with that of the prior art (DC), 6 times a day for 60 days.

The classic dry eye symptoms, i.e. smart, photophobia, foreign body sensation, and pain, were evaluated in all patients giving scores from 0 (no symptom) to 4 (serious symptom). Evaluations were conducted before treatment and after a 15, 30, and 60 days' treatment with the two preparations. The results of said trials on two of the aforesaid symptoms are shown in Tables 1 and 2, and the corresponding values are illustrated in FIGS. 2 to 5 attached hereto.

TABLE 2

Ocular symptomatology trials - Foreign body sensation (%)

| Symptom | basal | | 15 days | | 30 days | | 60 days | |
|---|---|---|---|---|---|---|---|---|
| | SVS20 | DC | SVS20 | DC | SVS20 | DC | SVS20 | DC |
| 4: very intense | 6 | 3 | 0 | 0 | 0 | 0 | 0 | 0 |
| 3: intense | 20 | 17 | 1 | 4 | 0 | 2 | 0 | 3 |
| 2: moderate | 28 | 42 | 13 | 35 | 2 | 15 | 0 | 6 |
| 1: light | 35 | 30 | 49 | 35 | 30 | 49 | 16 | 37 |
| 0: absent | 11 | 8 | 37 | 26 | 68 | 34 | 84 | 54 |

All aforesaid data provide evidence that the preparation of the invention, compared with that based on cellulose, brings about a more rapid and significant improvement in subjective symptomatology.

The same patients were also subjected to trials intended to evaluate the average values of tear film break-up time (BUT) and lacrimal secretion (Shirmer I) plus the corneo-conjunctival surface dyeing with 2% fluorescein and 1% Rose Bengal, to which a score of 1 to 8 was given. The results of said comparative examinations are shown in Table 3 and in the diagrams of FIGS. 6 to 9 attached hereto.

TABLE 3

Lacrimal functionality and stability plus corneo-conjunctival surface integrity trials

| Trial, unit | basal | | 15 days | | 30 days | | 60 days | |
|---|---|---|---|---|---|---|---|---|
| | SVS20 | DC | SVS20 | DC | SVS20 | DC | SVS20 | DC |
| BUT, sec | 3.12 | 3.51 | 5.87 | 4.91 | 7.15 | 5.74 | 8.64 | 6.4 |
| Schirmer I mm/5 min | 3.87 | 3.74 | 7.3 | 4.88 | 9.55 | 6.16 | 10.68 | 6.87 |
| fluorescin, score | 4.95 | 5.01 | 2.21 | 3.62 | 1.14 | 2.57 | 0.36 | 1.3 |
| Rose Bengal, score | 4.92 | 5.06 | 2.29 | 3.69 | 1.21 | 2.42 | 0.38 | 1.45 |

TABLE 1

Ocular symptomatology trials - Smart (%)

| Symptom | basal | | 15 days | | 30 days | | 60 days | |
|---|---|---|---|---|---|---|---|---|
| | SVS20 | DC | SVS20 | DC | SVS20 | DC | SVS20 | DC |
| 4: very intense | 2 | 2 | 0 | 0 | 0 | 0 | 0 | 0 |
| 3: intense | 37 | 27 | 1 | 4 | 0 | 0 | 0 | 0 |
| 2: moderate | 37 | 45 | 26 | 41 | 2 | 15 | 2 | 9 |
| 1: light | 17 | 19 | 50 | 40 | 43 | 54 | 22 | 42 |
| 0: absent | 7 | 7 | 23 | 15 | 55 | 31 | 76 | 49 |

All aforesaid trials prove that the treatment with the preparation of the the invention, compared with the treatment with preparation DC of the prior art, brings about a more rapid and significant improvement of the pathology being considered.

Besides being subjected to the general clinical trials mentioned above, the patients were also subdivided into two groups. The first group of 113 people was subjected to tear osmolarity trials at the beginning of the investigation and after a 15, 30, and 60 days' treatment. The values were recorded 30 minutes and 90 minutes after eyewash instillation. Tear samples for osmolarity determination were taken with a microcapillary pipette and according to a technique preventing reflex lacrimation. Osmolarity was measured by a properly modified cryoscopic osmometer Osmomat 30 (Gonotec, Berlin, Germany).

Figure 10:
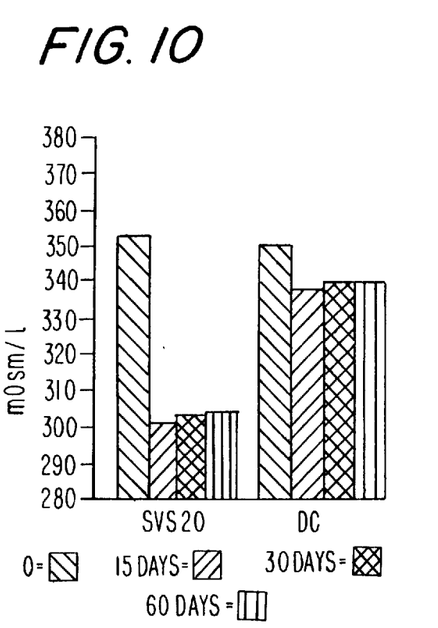
FIGS. 10 and 11 show the results of tear osmolarity measurements obtained using the preparation of the invention and the aforesaid commercial product of the prior art, 30 minutes and, respectively, 90 minutes after the last instillation.
Figure 11:
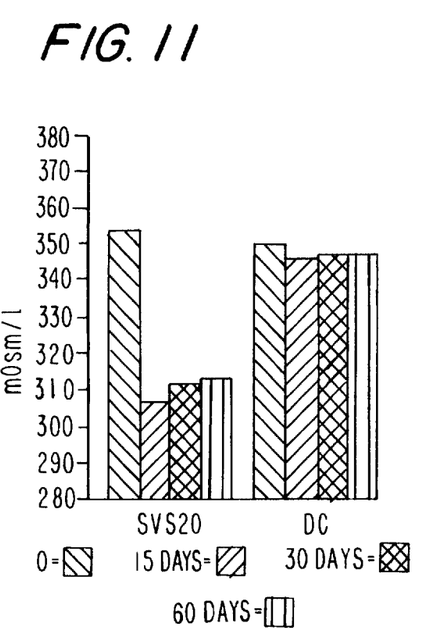
Figure 12:
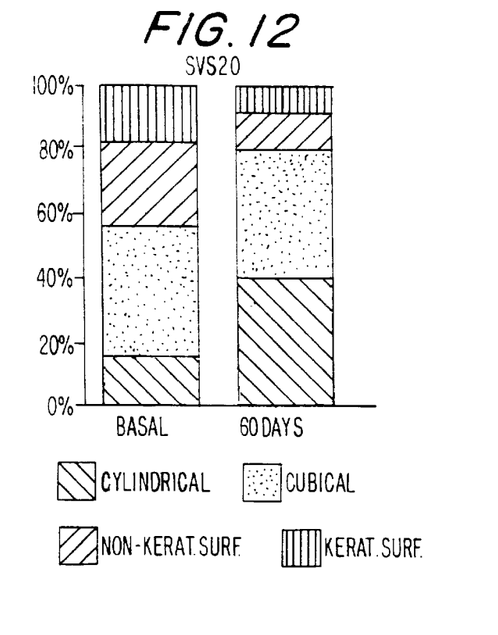
FIGS. 12 and 13 show the morphological distribution of epithelial cells before and after treatment with the preparation of the invention and, respectively, with the aforesaid commercial product of the prior art.
Figure 13:
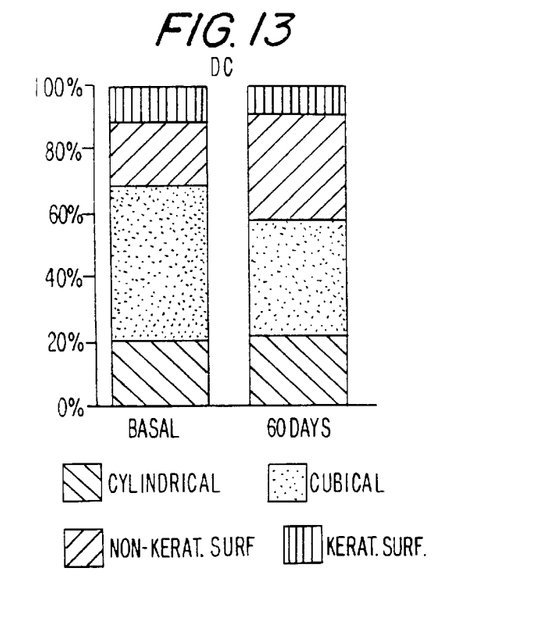
Figure 14:
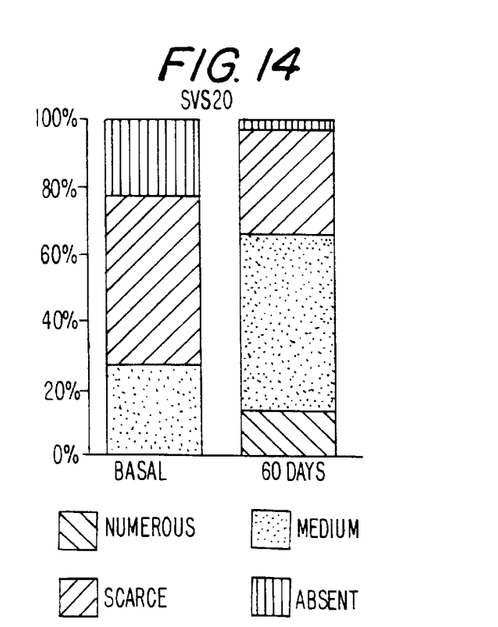
FIGS. 14 and 15 show the density distribution of goblet cells before and after treatment with the preparation of the invention and, respectively, with the aforesaid commercial product of the prior art.
Figure 15:
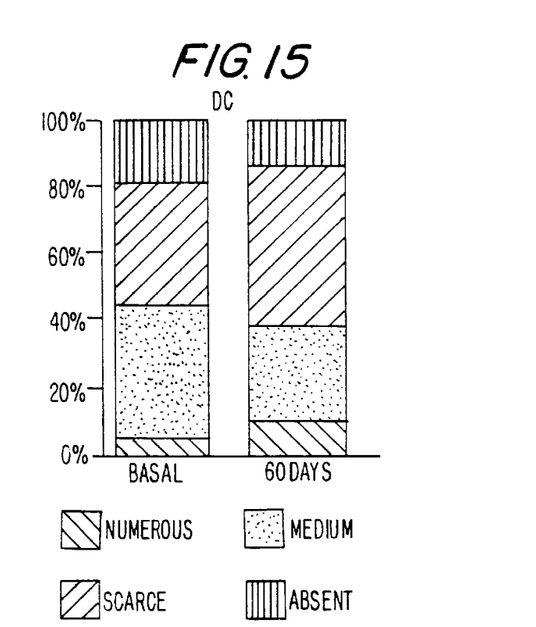
Figure 16:
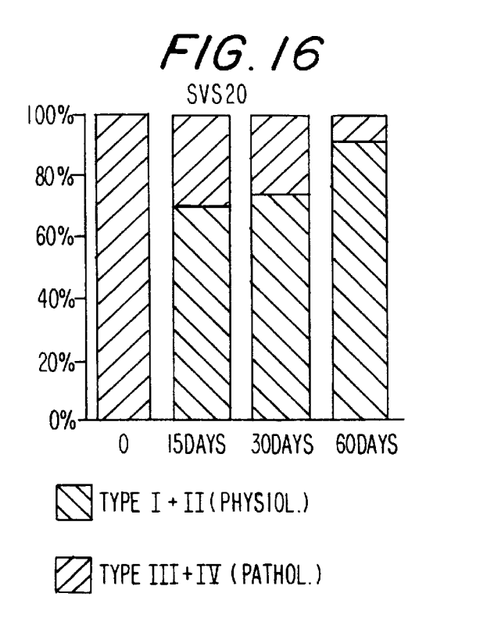
FIGS. 16 and 17 show the results of lacrimal mucus ferning tests, 30 minutes after instillation of the preparation of the invention and, respectively, of the aforesaid commercial product of the prior art.
Figure 17:
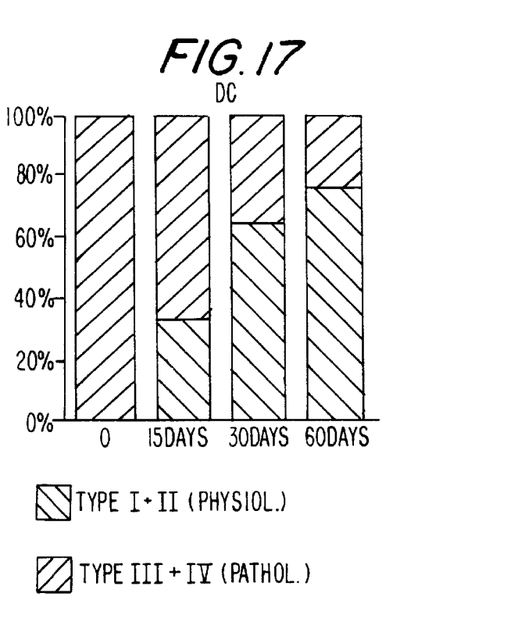
Figure 18:
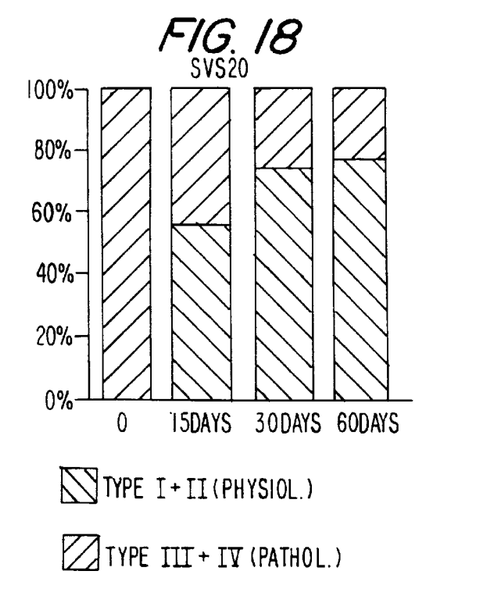
FIGS. 18 and 19 show the results of lacrimal mucus ferning tests, 90 minutes after instillation of the preparation of the invention and, respectively, of the aforesaid commercial product of the prior art.
Figure 19:
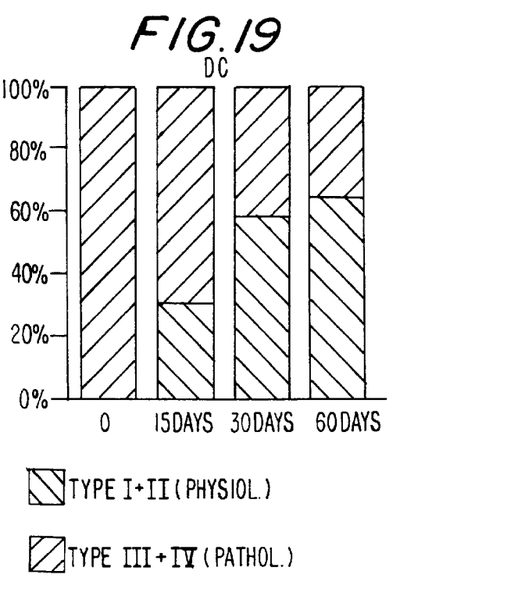

The average osmolarity values recorded in the two groups of patients treated with the drugs being compared are shown in Table 4 below and in FIGS. 10 and 11 attached hereto.

TABLE 4

Tear osmolarity average values (mOsm/l)

| Time from instillation | basal | | 15 days | | 30 days | | 60 days | |
|---|---|---|---|---|---|---|---|---|
| | SVS20 | DC | SVS20 | DC | SVS20 | DC | SVS20 | DC |
| 30 min | 353 | 350 | 301 | 338 | 303 | 340 | 304 | 340 |
| 90 min | 354 | 350 | 306 | 346 | 311 | 347 | 312 | 347 |

The second group of 92 patients was subjected both to cytology by impression and to tear ferning pattern tests. The former trial was conducted at the beginning of the investigation and after a 60 days' treatment, according to the technique described by D. J. Nelson, Cornea, 7 (1), 71–81 (1988), while tear ferning patterns were tested at the beginning of the investigation and after a 15, 30, and 60 days' treatment, 60 and 90 minutes after the last eyewash instillation. The latter test was performed as described by M. Rolando et al., Fortschr. Ophthalm., 83, 644–646, 1986.

The results of the trials conducted on the second group of patients are recapitulated in Tables 5 and 6 below and illustrated in the corresponding FIGS. 12–15 and 16–19 attached hereto.

In the present text, basal values are those recorded before treatment.

TABLE 5

Conjunctival cytology (%)

| | basal | | 60 days | |
|---|---|---|---|---|
| | SVS20 | DC | SVS20 | DC |
| Epithelial cells morphology | | | | |
| keratinized surface | 17 | 11 | 8 | 9 |
| non-keratinized surface | 26 | 20 | 11 | 33 |
| cubical | 41 | 49 | 41 | 36 |
| cylindrical | 16 | 20 | 40 | 22 |
| Goblet cells density | | | | |
| absent | 23 | 4 | 3 | 9 |
| scarce | 50 | 40 | 32 | 29 |
| medium | 27 | 36 | 52 | 47 |
| numerous | 0 | 20 | 13 | 15 |

TABLE 6

Lacrimal mucus ferning (%)

| | basal | | 15 days | | 30 days | | 60 days | |
|---|---|---|---|---|---|---|---|---|
| | SVS20 | DC | SVS20 | DC | SVS20 | DC | SVS20 | DC |
| 30 minutes | | | | | | | | |
| type III + IV | 100 | 100 | 30 | 71 | 26 | 42 | 9 | 36 |
| type I + II | 0 | 0 | 70 | 29 | 74 | 58 | 91 | 64 |
| 90 minutes | | | | | | | | |
| type III + IV | 100 | 100 | 44 | 67 | 26 | 36 | 23 | 23 |
| type I + II | 0 | 0 | 56 | 33 | 74 | 64 | 77 | 77 |

The increase in goblet cells and the improvement in epithelial cells morphology and in ferning pattern found in the samples treated with the preparation of the invention are better than those found in the samples treated with the preparation based on cellulose.

EXAMPLE 3

Clinical Trials and Comparison with Solutions Thickened with Sodium Hyaluronate as per Example 1

In the course of a further 2 months' clinical investigation, conducted according to an experimental plan providing for double blind trials on 24 patients with keratoconjunctivitis sicca, the effects of eyewash SVS20 of the invention were compared with the effects of an extemporaneous single dose 0.25% solution of sodium hyaluronate, isotonic with lacrimal gland fluid, containing sodium chloride alone, corresponding to preparation SO9 as per Example 1.

Both products were administered at a dose rate of 1 drop/eye 6 times a day. The results obtained proved that preparation SVS20 is effective for bringing the tear film osmolarity to physiological levels up to 90 minutes from instillation, stabilizing the precorneal film, while significantly increasing BUT and Shirmer I values, and remarkably improving the morphology of epithelial cells and the density of goblet cells. Conversely, in the patients treated with SO9, the osmolarity remained within pathological limits while a cytological examination showed that, after a 60 days' treatment, the conjunctival surface, compared with basal control, was nearly unmodified.

Figure 20:
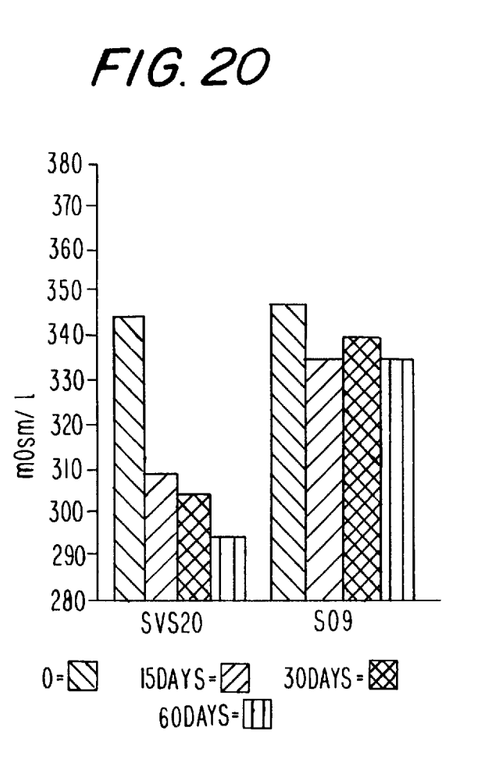
FIGS. 20 and 21 show the results of tear osmolarity measurements obtained using the preparation of the invention and the product of the prior art as per FIG. 1, 30 minutes and, respectively, 90 minutes after the latest instillation.
Figure 21:
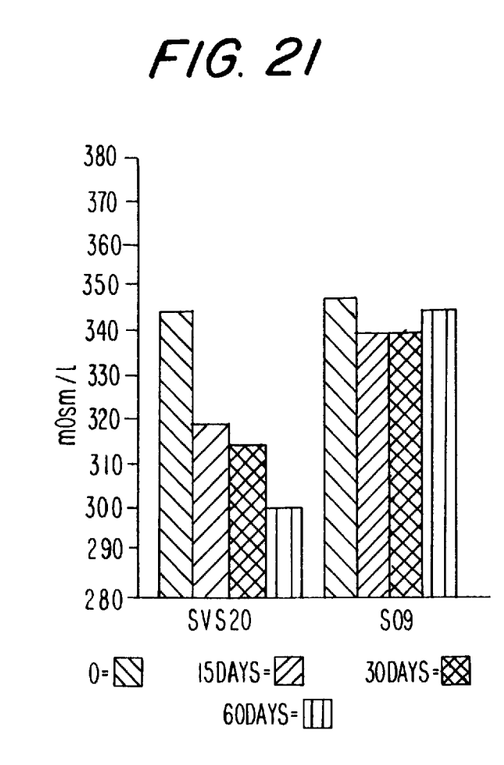
Figure 22:
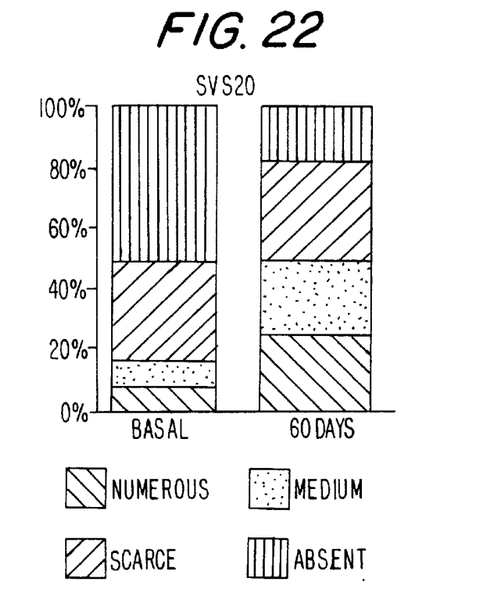
FIGS. 22 and 23 show the density distribution of goblet cells before and after treatment with the preparation of the invention and, respectively, with the aforesaid product of the prior art as per FIG. 1.
Figure 23:
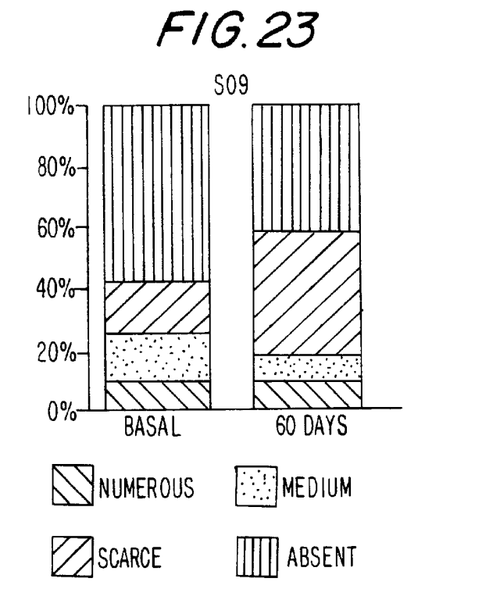
Figure 24:
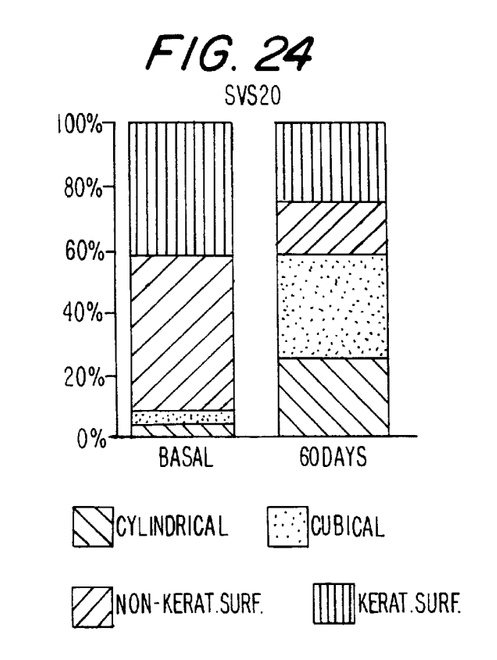
FIGS. 24 and 25 show the morphological distribution of epithelial cells before and after treatment with the preparation of the invention and, respectively, with the aforesaid product of the prior art as per FIG. 1.
Figure 25:
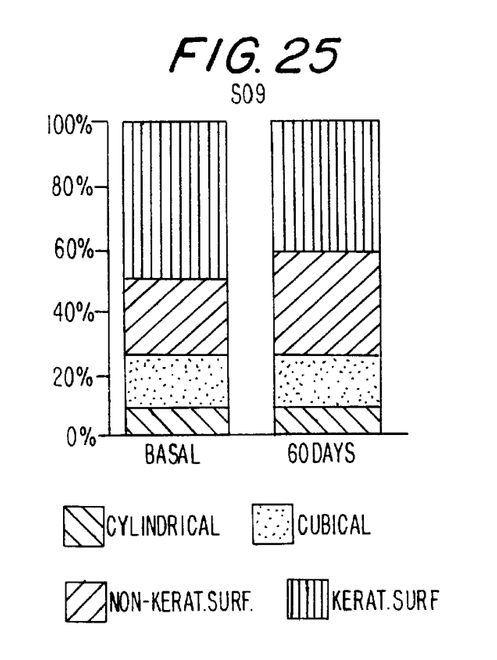

The results of tear osmolarity measurements conducted as described in Example 2 are shown in Table 7 below and in FIGS. 20 and 21 attached hereto.

TABLE 7

| | Tear osmolarity average values (mOsm/l) | | | | | | | |
|---|---|---|---|---|---|---|---|---|
| | basal | | 15 days | | 30 days | | 60 days | |
| Time from instillation | SVS20 | S09 | SVS20 | S09 | SVS20 | S09 | SVS20 | S09 |
| 30 min | 345 | 348 | 310 | 335 | 305 | 340 | 295 | 335 |
| 90 min | 345 | 348 | 320 | 340 | 315 | 340 | 300 | 345 |

The results of the cytological examination conducted as described in Example 2 are shown in Table 8 below and in FIGS. 22–25 attached hereto.

TABLE 8

| | Conjunctival cytology (%) | | | |
|---|---|---|---|---|
| | basal | | 60 days | |
| | SVS20 | DC | SVS20 | DC |
| Goblet cells density | | | | |
| absent | 50 | 58 | 17 | 42 |
| scarce | 34 | 17 | 33 | 42 |
| medium | 8 | 17 | 25 | 8 |
| numerous | 8 | 8 | 25 | 8 |
| Epithelial cells morphology | | | | |
| keratinized surface | 42 | 50 | 25 | 42 |
| non-keratinized surface | 50 | 25 | 17 | 33 |
| cubical | 4 | 17 | 33 | 17 |
| cylindrical | 4 | 8 | 25 | 8 |

The results of the clinical trials described above suggest that eyewash SVS20, which is formulated with sodium hyaluronate in a vehicle containing ions essential for a physiological cellular metabolism, significantly stabilizes the tear film and restores a quali-quantitative equilibrium in the precorneal environment, thus preventing the epithelial cells to degenerate into pathological functional and morphological states and the goblet cells to attain a higher density.

The presence of a non-Newtonian polymer, as sodium hyaluronate is, stabilizes the tear film and delays tear evaporation, reduces the transmission on the eye surface of rubbing stresses produced by eyelids during wink, and is well tolerated.

The present invention has been described with particular reference to some of its exemplary embodiments. However, variations and modifications may be effected by those skilled in the art without departing from the scope of the invention.

I claim:

1. An ophthalmic aqueous preparation for use as artificial tear containing a viscosity thickener consisting of at least one hyaluronic acid salt, at a concentration of 0.05 to 2% by weight, as well as the following quantities of ionic species: 40–95 mmol/l of sodium ions, 12–28 mmol/l of potassium ions, 0.4–1,5 mmol/l of calcium ions, 0.4–1.0 mmol/l of magnesium ions, 50–100 mmol/l of chloride ions, 7–20 mmol/l of phosphate ions, 0.7–2.5 mmol/l of citrate ions, and water,
said composition having a viscosity versus shear rate, measured at 32° C. from 10.0 to 200.0 cps at a shear rate of 2 $sec^{-1}$ and from 10 to 5 cps at a shear rate of 1000 $sec^{-1}$, and an osmolarity from 140 to 280 mOsm/l.

2. The preparation according to claim 1, further containing at least 7 mmol/l of acetate ion.

3. The preparation according to claim 1, further containing at least 5 mmol/l of bicarbonate ion.

4. The preparation according to claim 1, further containing at least 1 mmol/l of EDTA.

5. The preparation according to claim 1, wherein said hyaluronic acid salt is sodium hyaluronate having molecular weight of 500,000 to 4,000,000 daltons.

6. The preparation according to claim 1, having pH of 6.8 to 7.6.

7. An ophthalmic aqueous preparation for use as artificial tear, having the following composition:

| | mg/100 ml | mmol/l |
|---|---|---|
| sodium hyaluronate | 250 | ~6.2 |
| NaCl | 279.2 | 47.77 |
| KCl | 103.3 | 13.85 |
| $Na_2HPO^4.12H_2O$ | 322.2 | 9.0 |
| $Na_3$ citrate | 26.0 | 1.05 |
| $MgCl_2.6H_2O$ | 9.2 | 0.45 |
| $CaCl_2.2H_2O$ | 6.9 | 0.6 | wherein sodium hyaluronate has molecular weight 800,000–1,600,000, and the solution has pH=7.32 and osmolarity=150 mOsm/l, and a viscosity of 28 Cps at a shear rate of 2 $sec^{-1}$.

8. A therapeutic method for the treatment of keratoconjuctivitis sicca or of eye irritations, which comprises instillation in the conjuctival sac of a subject in a need of such treatment a therapeutically effective amount of an ophtalmic preparation as claimed in claim 1.

9. The therapeutic method as claimed in claim 8, wherein eye irritations are those caused by environmental conditions or contact lenses.

10. The preparation according to claim 1, further containing dextrose.

11. The preparation according to claim 1, further containing preservatives.

12. The preparation according to claim 11, containing sodium ethylmercurithiosalicilate as a preservative.

13. The preparation according to claim 1, wherein said hyaluronic acid salt is sodium hyaluronate having molecular weight of 500,000 to 8,000,000 daltons.

14. The therapeutic method as claimed in claim 8, which comprises administering 1–2 drops per eye, from 4 to 8 times a day.

15. An ophthalmic aqueous preparation for use as artificial tear in the treatment of a disease selected from the group consisting of dry eye syndrome and a state of eye irritation, containing a viscosity thickener consisting of at least one hyaluronic acid salt, at a concentration of 0.05 to 2% by weight, as well as the following quantities of ionic species: 49–95 mmol/l of sodium ions, 12–28 mmol/l of potassium ions, 0.4–1,5 mmol/l of calcium ions, 0.4–1.0 mmol/l of magnesium ions, 50–100 mmol/l of chloride ions, 7–20 mmol/l of phosphate ions, 0.7–2.5 mmol/l of citrate ions, and water, said composition having a viscosity versus shear rate, measured at 32° C., from 10.0 to 200.0 cps at a shear rate of 2 $sec^{-1}$ and from 10 to 5 cps at a shear rate of 1000 $sec^{-1}$, and an osmolarity from 140 to 280 mOsm/l.

16. The preparation according to claim 15, wherein the eye irritations are those caused by environmental conditions or contact lenses.

17. The preparation according to claim 15, further containing at least one additional ingredient selected from the group consisting of: at least 7 mmol/l of acetate ion, at least 5 mmol/l of bicarbonate ion and at least 1 mmol/l of EDTA.

18. The preparation according to claim 15, wherein said hyaluronic acid salt is sodium hyaluronate having molecular weight of 500,000 to 8,000,000 daltons.

19. The preparation according to claim 15, wherein said hyaluronic acid salt is sodium hyaluronate having molecular weight of 500,000 to 4,000,000 daltons.

20. The preparation as claimed in claim 15, which has a pH from 6.8 to 7.6.

21. A therapeutic method for the treatment of keratoconjuctivitis sicca or of eye irritations, which comprises instilling in the conjuctival sac of a subject in a need of such treatment a therapeutically effective amount of an ophthalmic preparation as claimed in claim 15.

22. The therapeutic method as claimed in claim 21, wherein eye irritations are those caused by environmental conditions or contact lenses.

23. The therapeutic method as claimed in claim 21, which comprises administering 1–2 drops per eye, from 4 to 8 times a day.

24. An ophthalmic aqueous preparation for use as artificial tear consisting essentially of at least one hyaluronic acid salt, at a concentration of 0.05 to 2% by weight, as well as the following quantities of ionic species: 40–95 mmol/l of sodium ions, 12–28 mmol/l of potassium ions, 0.4–1,5 mmol/l of calcium ions, 0.4–1.0 mmol/l of magnesium ions, 50–100 mmol/l of chloride ions, 7–20 mmol/l of phosphate ions, 0.7–2.5 mmol/l of citrate ions, and water, said composition having a viscosity versus shear rate, measured at 32° C., from 10.0 to 200.0 cps at a shear rate of 2 $sec^{-1}$ and from 10 to 5 cps at a shear rate of 1000 $sec^{-1}$, and an osmolarity from 140 to 280 mOsm/l.

25. The preparation as claimed in claim 24, for use in the treatment of an eye irritation state selected from the group consisting of dry eye syndrome and of eye irritations.

26. The preparation according to claim 24, wherein the eye irritations are those caused by environmental conditions or contact lenses.

27. The preparation as claimed in claim 24, which has a pH from 6.8 to 7.6.

28. The preparation according to claim 24, wherein said hyaluronic acid salt is sodium hyaluronate having molecular weight of 500,000 to 8,000,000 daltons.

29. The preparation according to claim 24, wherein said hyaluronic acid salt is sodium hyaluronate having molecular weight of 500,000 to 4,000,000 daltons.

30. The preparation according to claim 24, further containing at least one additional ingredient selected from the group consisting of at least 7 mmol/l of acetate ion, at least 5 mmol/l of bicarbonate ion and at least 1 mmol/l of EDTA.

31. A therapeutic method for the treatment of keratoconjuctivitis sicca or of eye irritations, which comprises instilling in the conjuctival sac of a subject in need of such treatment a therapeutically effective amount of an ophthalmic preparation as claimed in claim 15.

32. The therapeutic method as claimed in claim 31, wherein eye irritations are those caused by environmental conditions or contact lenses.

33. The therapeutic method as claimed in claim 31, which comprises administering 1–2 drops per eye, from 4 to 8 times a day.

* * * * *